United States Patent
Wu et al.

(10) Patent No.: US 8,291,908 B2
(45) Date of Patent: Oct. 23, 2012

(54) DEVICE FOR POSITIONING TRACHEOSTOMY TUBE

(76) Inventors: Ching-Yang Wu, Linkou Township, Taipei County (TW); Yun-Hen Liu, Guishan Shiang (TW); Po-Jen Ko, Taipei (TW)

(*) Notice: Subject to any disclaimer, the term of this patent is extended or adjusted under 35 U.S.C. 154(b) by 643 days.

(21) Appl. No.: 12/508,654

(22) Filed: Jul. 24, 2009

(65) Prior Publication Data

US 2011/0017208 A1 Jan. 27, 2011

(51) Int. Cl.
*A61M 16/00* (2006.01)

(52) U.S. Cl. .......... 128/207.14; 128/207.13; 128/207.15

(58) Field of Classification Search ............. 128/207.15, 128/207.14, 200.13, 200.14; 606/108
See application file for complete search history.

(56) References Cited

U.S. PATENT DOCUMENTS

| | | | | |
|---|---|---|---|---|
| 6,475,232 | B1* | 11/2002 | Babbs et al. | 623/1.13 |
| 7,691,138 | B2* | 4/2010 | Stenzel et al. | 623/1.11 |
| 7,921,847 | B2* | 4/2011 | Totz | 128/207.15 |
| 2007/0017527 | A1* | 1/2007 | Totz | 128/207.15 |
| 2010/0286791 | A1* | 11/2010 | Goldsmith | 623/23.7 |

* cited by examiner

*Primary Examiner* — Glenn Richman

(57) ABSTRACT

A device for positioning a tracheostomy tube includes a tracheostomy tube and a tracheostomy tube protecting membrane. The tracheostomy tube protecting membrane includes a tearing line portion formed at two sides of the tracheostomy tube protecting membrane. The tracheostomy tube protecting membrane is used for mounting in a trachea of a patient to form a positioning path for the tracheostomy tube. The tearing line portion is used for being torn open and removed. The tracheostomy tube protecting membrane is mounted in a trachea of a patient first. The tracheostomy tube protecting membrane can effectively protect the trachea of the patient.

5 Claims, 7 Drawing Sheets

DEVICE FOR POSITIONING TRACHEOSTOMY TUBE

BACKGROUND OF THE INVENTION

1. Field of Invention

The invention relates to a device for positioning a tracheostomy tube and, more particularly, to a device for positioning the tracheostomy tube that can effectively protect a trachea of a patient.

2. Description of Related Art

With the rapid progress of medical skill, supplying enough oxygen to the patients with respiratory failure is possible by utilizing a respirator (breather) or portable oxygen providing equipment. Before using the equipment, maintaining an effective and safe respiratory passage for patients is very important. Thus, it is necessary to perform tracheotomy surgery and implant the tracheostomy tube for patients who need to use auxiliary breathing equipment to support their breathing for a long period. However, the method disclosed in the prior art about mounting the tracheostomy tube into the trachea may cause trachea mucous injury, bleeding of the trachea or a fatal innominate artery injury, because of an inexperienced operator or a smaller incision. On the contrary, a wider incision for operation safety may result in subcutaneous emphysema and poor tracheostomy healing.

In the present market, there is a tracheostomy tube assembly, named the Blue-Rhino, utilizing a dilator passing through the skin along with the wire to create a subcutaneous passage and implanting the tracheostomy tube. However, the Blue-Rhino tube assembly is difficult to operate on patients with nodular goiter or tracheal deviation. Besides, the cost of the Blue-Rhino tube assembly is not less than conventional tracheostomy surgery, so it is still unable to replace tracheostomy surgery with a small incision. Therefore, the need to improve the structure of the tracheostomy tube and simplify the surgery procedure in order to prevent possible complications after surgery still exists.

Referring to FIG. 7, the conventional tracheostomy tube typically comprises a tracheostomy tube body 50 and a balloon 60. The tracheostomy tube body 50 includes a first end 51 and a second end 52. The balloon 60 is mounted on the outside surface of the first end 51. However, the balloon 60 of the conventional tracheostomy tube is easily broken when mounting, requiring implantation again. Besides, when implanting the first end 51 of the conventional tracheostomy tube, it is very easy to injure the trachea 71 of the patient 70. Thus, the need for improvement still exists.

SUMMARY OF THE INVENTION

It is therefore one object of the invention to provide a device for positioning a tracheostomy tube including a tracheostomy tube and a tracheostomy tube protecting membrane. The tracheostomy tube protecting membrane comprises a tearing line portion formed at two sides of the tracheostomy tube protecting membrane. The tracheostomy tube protecting membrane is used for mounting in a trachea of a patient to form a positioning path for the tracheostomy tube. The tearing line portion is used for being torn open and removed.

In a first aspect of the invention, the tracheostomy tube comprises a tube body and a balloon. The tracheostomy tube has a first end and a second end. The balloon is mounted on the first end of the tracheostomy tube.

In a second aspect of the invention, the tracheostomy tube protecting membrane is a plastic thin membrane.

In a third aspect of the invention, the tracheostomy tube has a first length. The tracheostomy tube protecting membrane has a second length. The second length is greater than the first length.

In a fourth aspect of the invention, the tracheostomy tube protecting membrane comprises a third end and an fourth end. The third end has a first opening. The fourth end has a second opening. The first opening is greater than the second opening.

In a fifth aspect of the invention, the device further comprises a connector. The connector is mounted on the tracheostomy tube protecting membrane.

By utilizing the invention, the following advantages are obtained. First, the present invention utilizes the tracheostomy tube protecting membrane to be mounted in a trachea of a patient first. It can effectively avoid the balloon of the tracheostomy tube breaking and can decrease operation times. The invention can facilitate surgery and can greatly increase the surgery success probability. Moreover, the present invention utilizes the tracheostomy tube protecting membrane to be mounted in a trachea of a patient first. The tracheostomy tube protecting membrane can effectively protect the trachea of the patient. It can effectively prevent one end of the tracheostomy tube from injuring the trachea of the patient when the conventional tracheostomy tube is mounted. In other words, the tracheostomy tube protecting membrane can effectively avoid trachea injury.

The invention will become more obvious from the following description when taken in connection with the accompanying drawings.

DETAILED DESCRIPTION OF THE INVENTION

Figure 1:
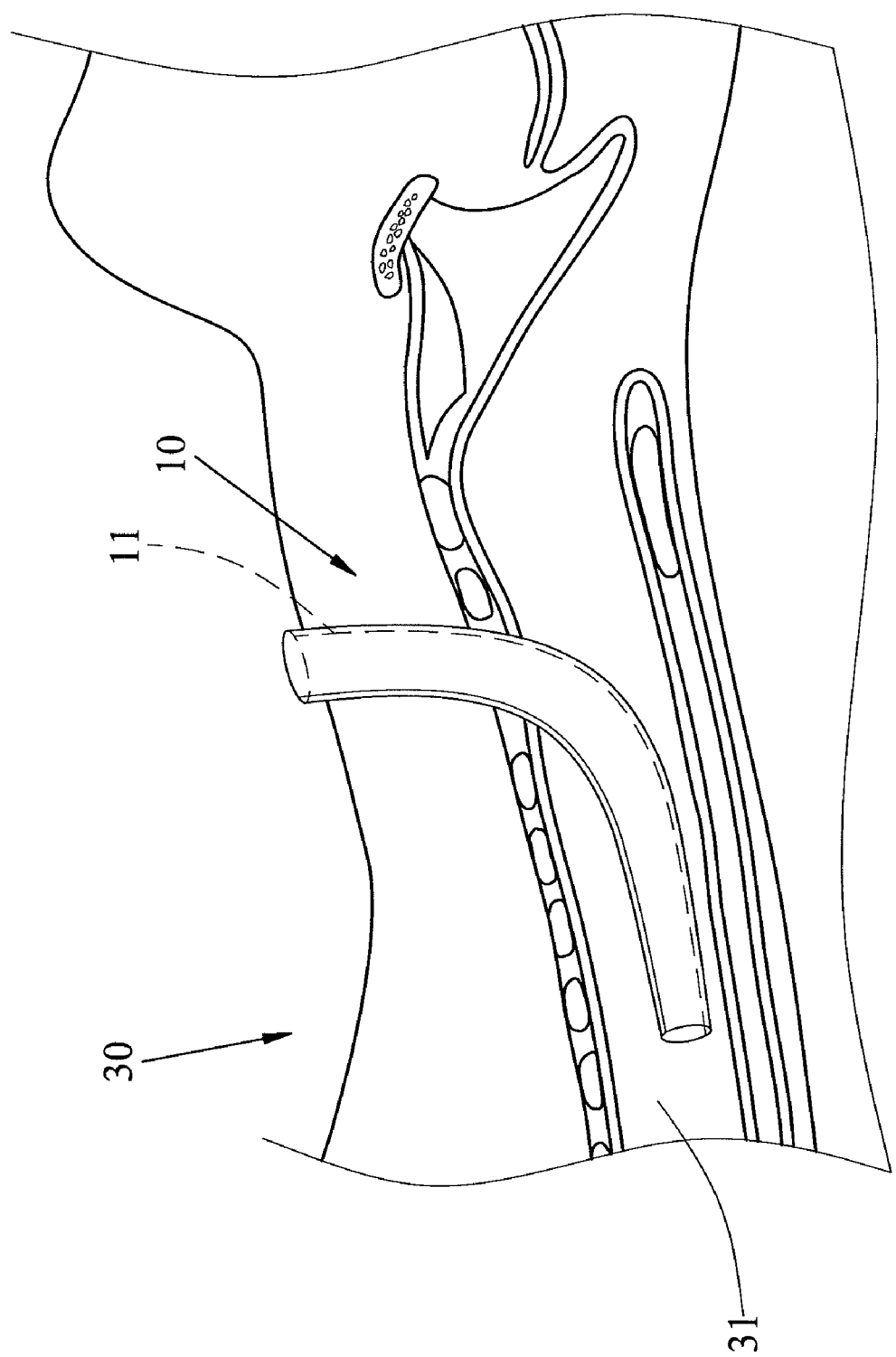
FIG. 1 is an operational view showing a tracheostomy tube protecting membrane mounted in a trachea of a patient in accordance with the present invention.
Figure 2:
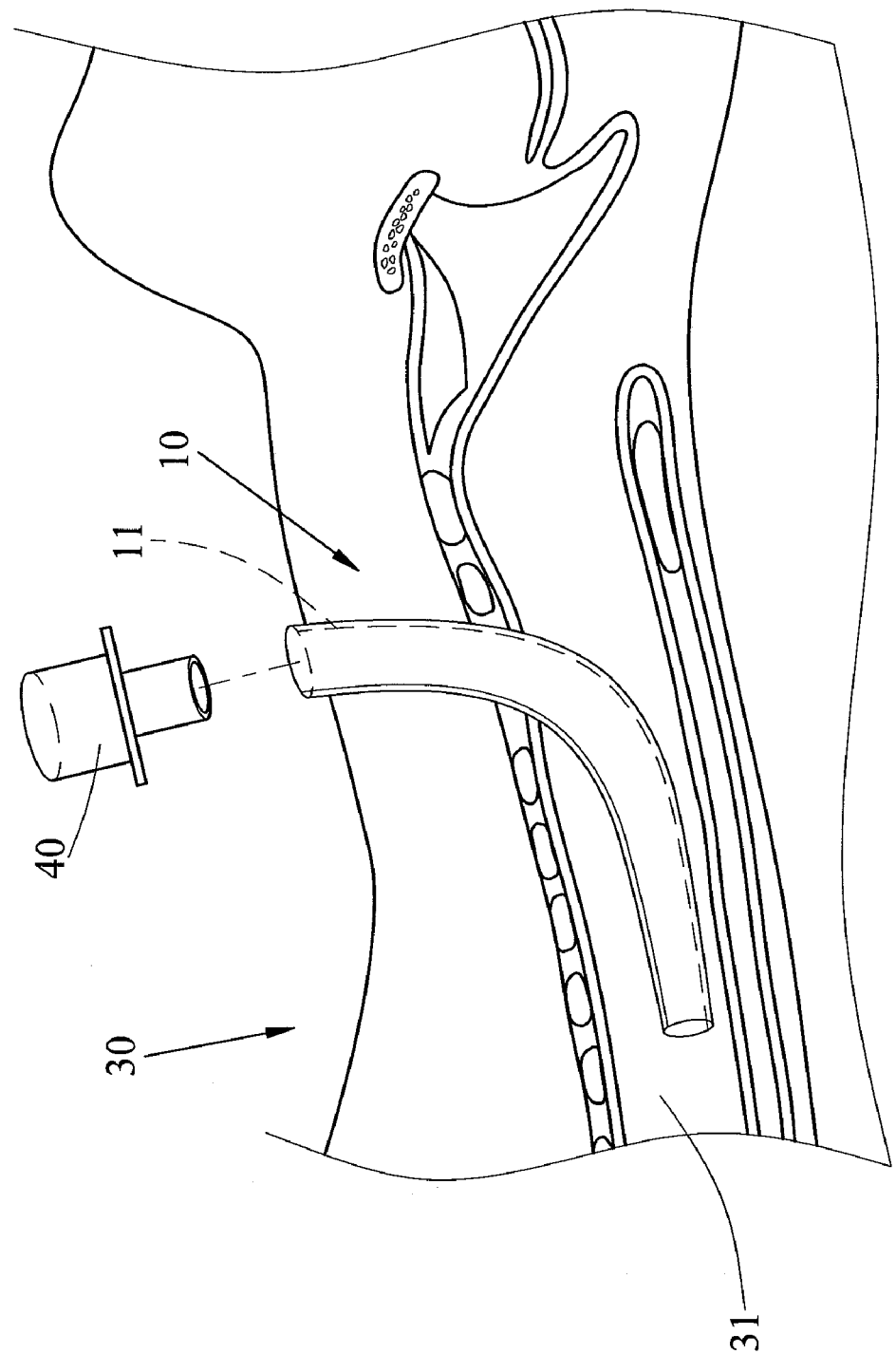
FIG. 2 is an exploded view showing a connector mounted to the tracheostomy tube protecting membrane in accordance with the present invention.
Figure 3:
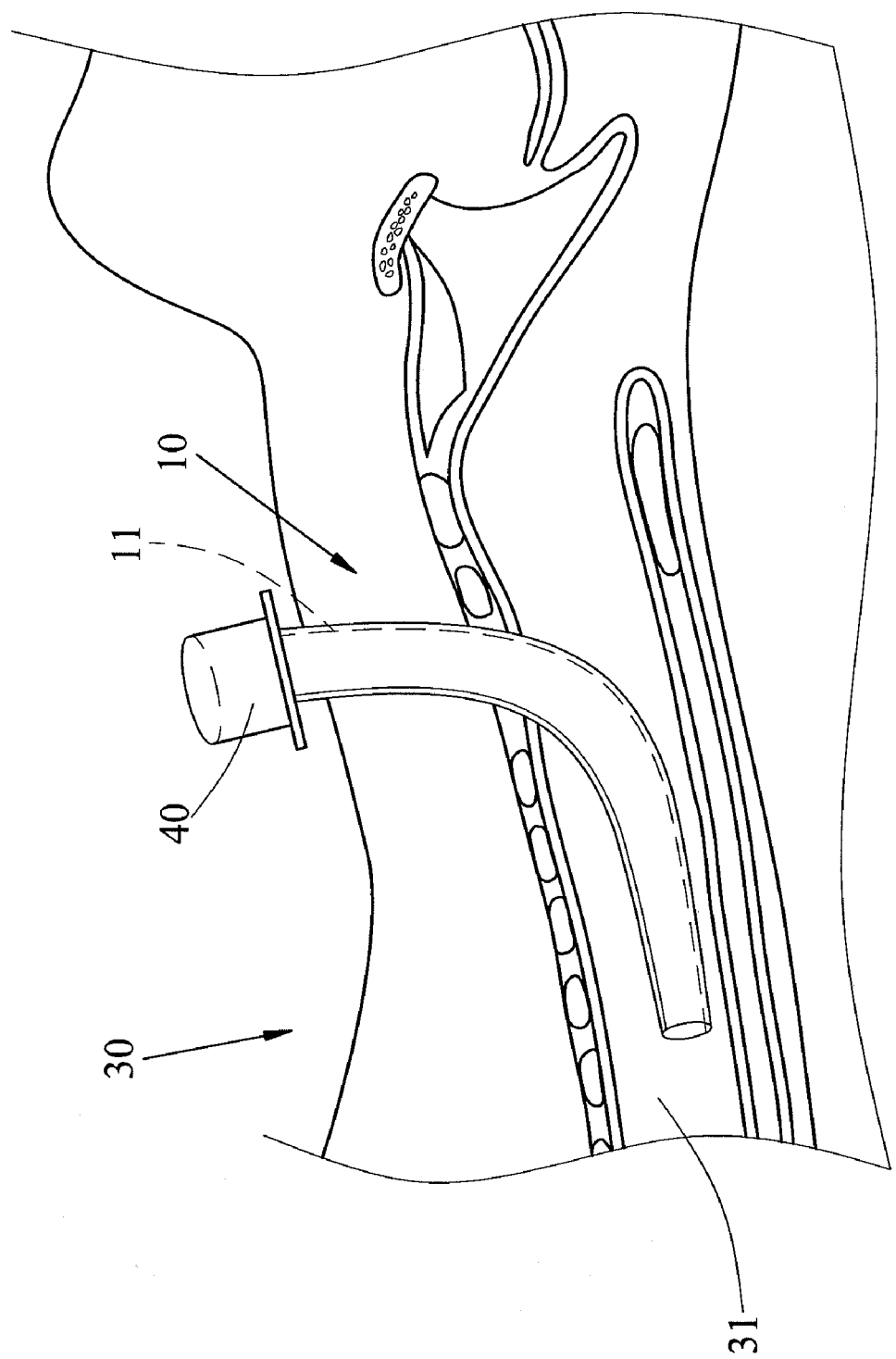
FIG. 3 is an operational view showing the connector mounted on the tracheostomy tube protecting membrane in accordance with the present invention.
Figure 4:
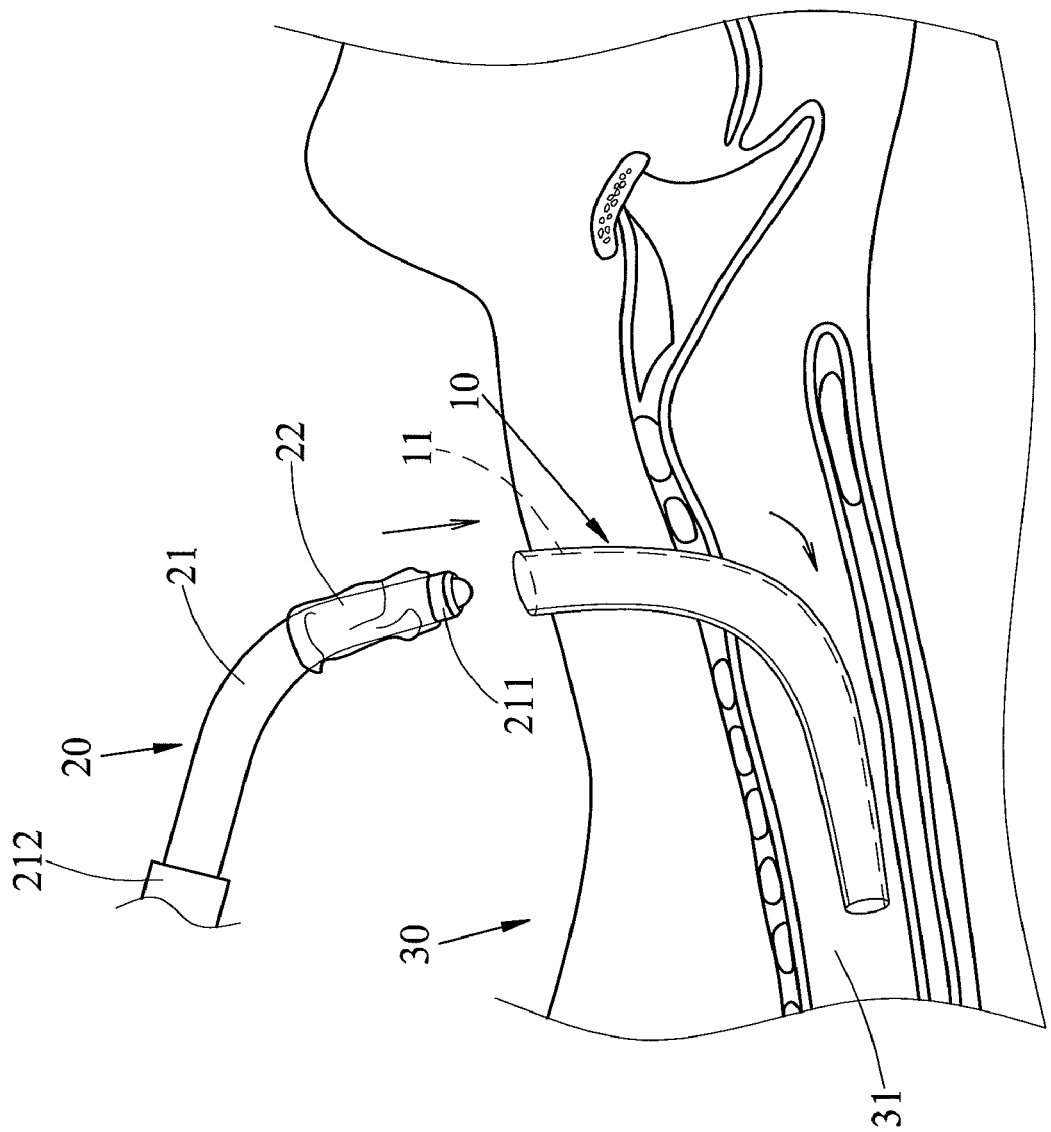
FIG. 4 is another operational view showing the tracheostomy tube mounted to the tracheostomy tube protecting membrane in accordance with the present invention.
Figure 5:
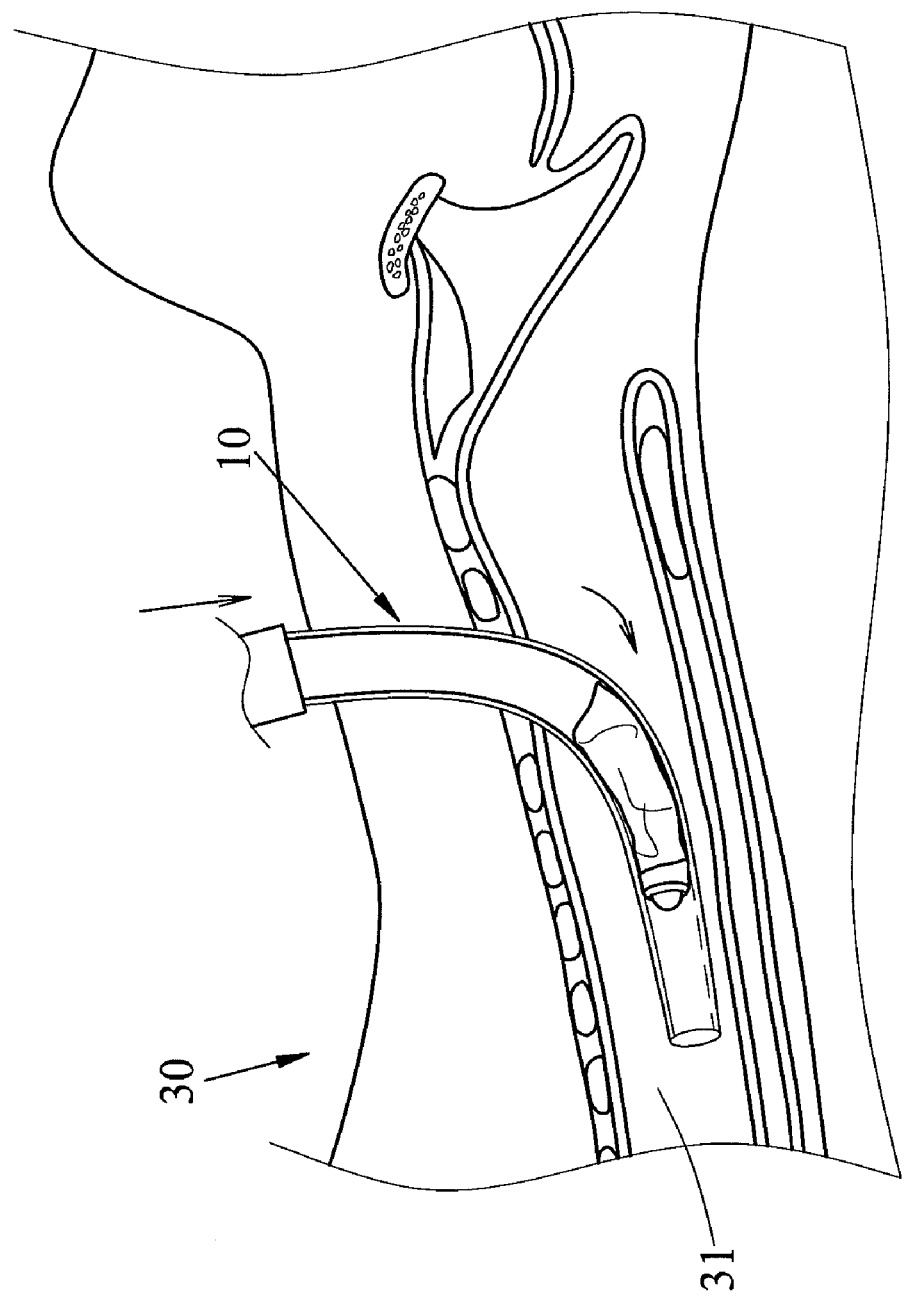
FIG. 5 is another operational view showing the tracheostomy tube mounted in the tracheostomy tube protecting membrane in accordance with the present invention.
Figure 6:
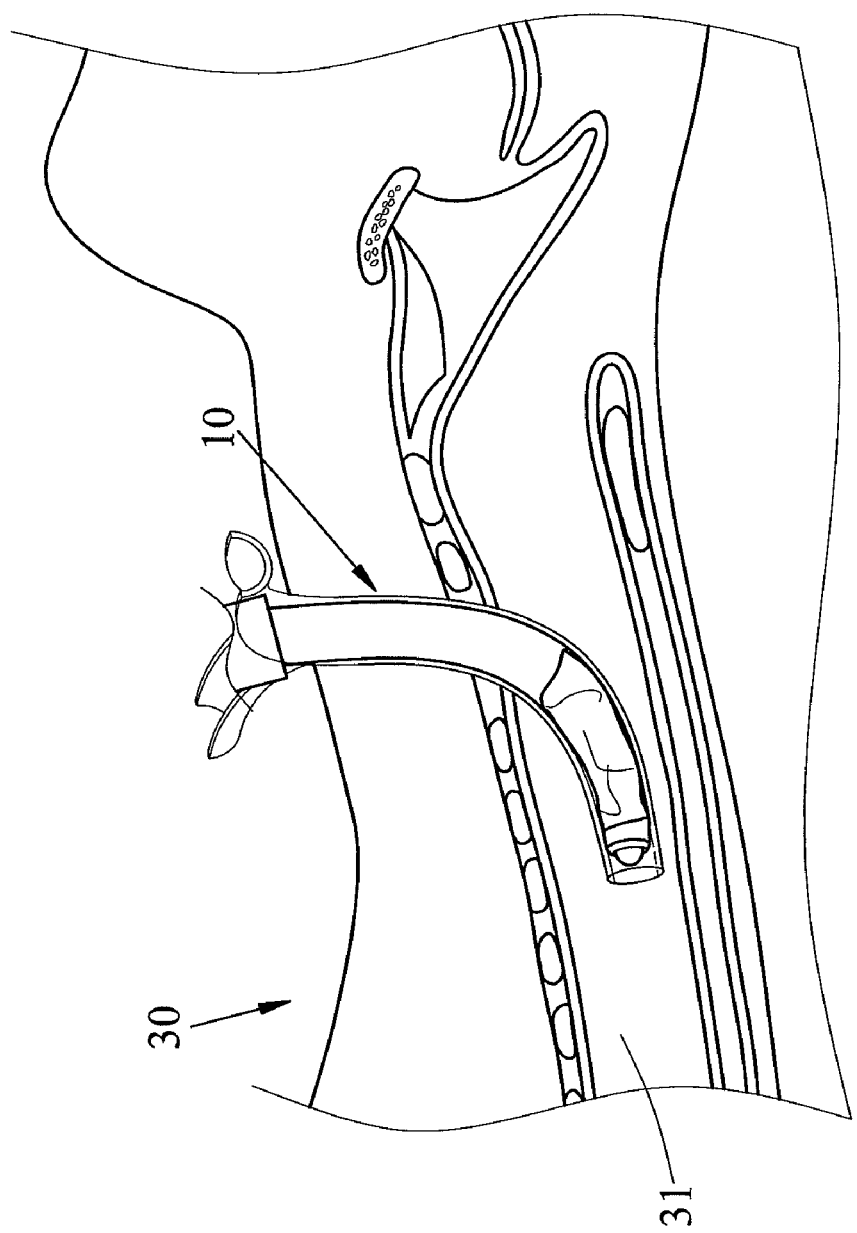
FIG. 6 is an operational view showing how to tear open and remove the tracheostomy tube protecting membrane in accordance with the present invention.
Figure 7:
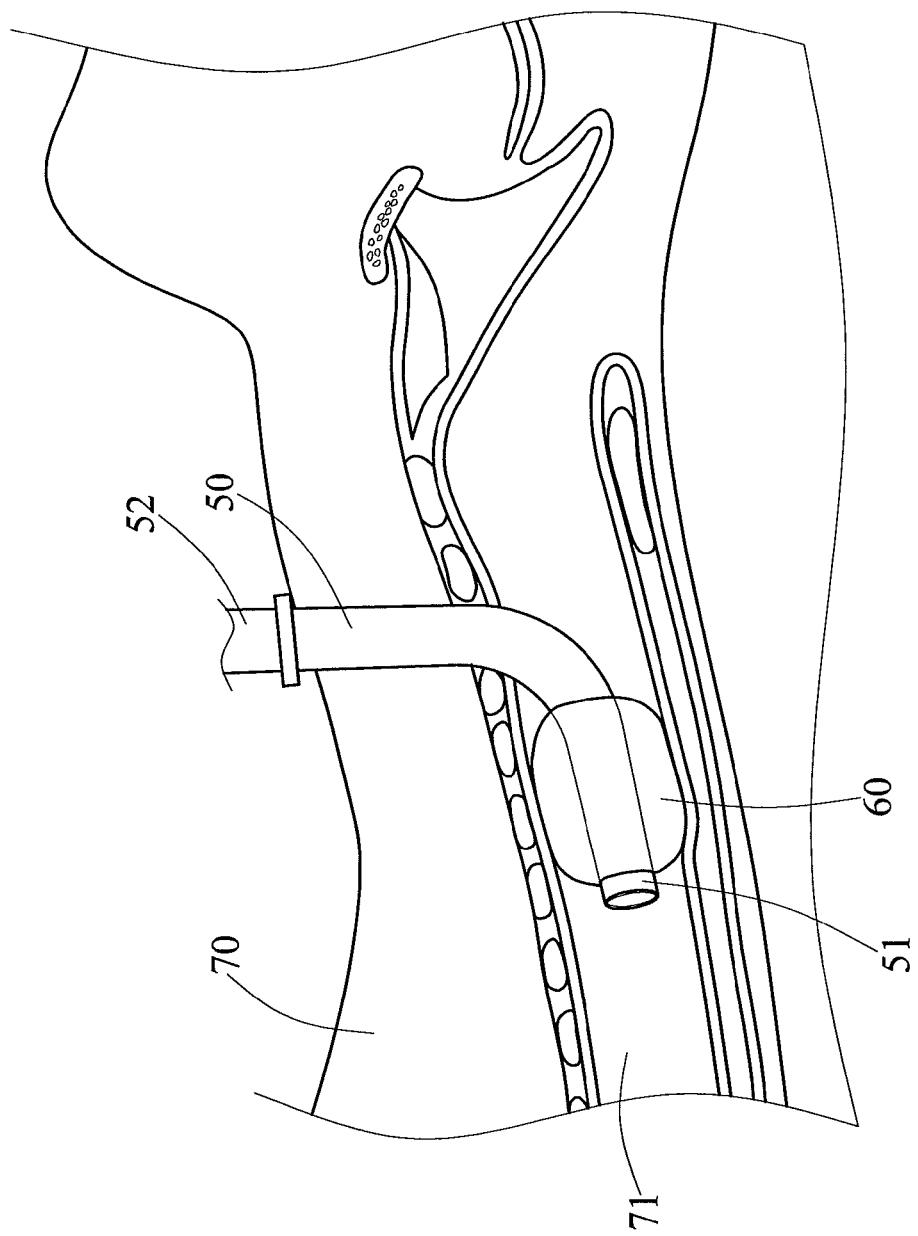
FIG. 7 is an operational view of a conventional tracheostomy tube.

Referring to FIGS. 1 to 6, a device for positioning a tracheostomy tube comprises a tracheostomy tube protecting membrane 10 and a tracheostomy tube 20. The tracheostomy tube protecting membrane 10 comprises a tearing line portion 11 formed at two sides of the tracheostomy tube protecting membrane 10. The tracheostomy tube protecting membrane 10 is used for mounting in a trachea 31 of a patient 30 to form a positioning path for the tracheostomy tube 20. The tearing line portion 11 is used for being torn open and removed.

Preferably, the tracheostomy tube 20 comprises a tube body 21 and a balloon 22. The tracheostomy tube 20 has a first end 211 and a second end 212. The balloon 22 is mounted on the first end 211 of the tracheostomy tube 20.

Preferably, the tracheostomy tube protecting membrane 10 is a plastic membrane.

Preferably, the tracheostomy tube 20 has a first length. The tracheostomy tube protecting membrane 10 has a second length. The second length is greater than the first length.

Preferably, the tracheostomy tube protecting membrane 10 comprises a third end and an fourth end; the third end has a first bore; the fourth end has a second bore; the first bore is greater than the second bore.

Preferably, the tracheostomy tube protecting membrane 10 comprises a third end and an fourth end. The third end has a first opening. The fourth end has a second opening. The first opening is greater than the second opening.

A tracheostomy tube insertion method in accordance with the invention is illustrated. The method comprises the following steps:

a. Operational procedure in a tracheotomy is the same as the prior art.

b. First, cut open the trachea 31 of the patient 30. Second, utilize a medical instrument to open the trachea 31. Third, implant the tracheostomy tube protecting membrane 10 into the trachea 31 and operate with naked eyes. Fourth, sleeve the tracheostomy tube 20 with a blunt inner pipe and insert the tracheostomy tube 20 with the blunt inner pipe along the tracheostomy tube protecting membrane 10. The method disclosed in the prior art typically utilizes the tracheostomy tube 20 sleeved with the blunt inner pipe mounted into the trachea 31 of the patient 30. While the tracheostomy tube 20 is perpendicular to the trachea 31, turn the tracheostomy tube 20 at an angle in the trachea 31. In this kind of operation, it may injure the mucous membrane of the trachea 31 and lead to the bleeding of the trachea 31. Besides, if the tracheostomy tube 20 isn't mounted in the trachea 31 well, it may also result in an innominate artery injury. In comparison, the present invention provides the tracheostomy tube protecting membrane 10 to protect the trachea 31 of the patient 30 effectively.

c. After finishing the mounting steps, tear open the tracheostomy tube protecting membrane 10 along the tearing line portion 11 into two pieces.

d. Fix the tracheostomy tube 20 in the trachea 31 of the patient 30.

If the patient 30 is in a poor oxygenation condition during the tracheostomy, the present invention utilizes the connector 40 to mount on the tracheostomy tube protecting membrane 10 for supplying enough oxygen to the patient 30. When the patient 30 is in a normal oxygenation condition, remove the connector 40. Then, mount the tracheostomy tube 20 in the tracheostomy tube protecting membrane 10 to finish the surgery. When the connector 40 is mounted on the tracheostomy tube protecting membrane 10, the connector 40 can be connected to a snake-shaped pipe of a respirator to supply oxygen. Therefore, the connector 40 can be used for supplying oxygen to the patient 30 in an emergency when the patient 30 is in a poor oxygenation condition.

By utilizing the invention, the following advantages are obtained. First, the present invention utilizes the tracheostomy tube protecting membrane to be mounted in a trachea of a patient first. It can effectively avoid the balloon of the tracheostomy tube breaking and can decrease operation times. The invention can facilitate surgery and can greatly increase the surgery success probability. Moreover, the present invention utilizes the tracheostomy tube protecting membrane to be mounted in a trachea of a patient first. The tracheostomy tube protecting membrane can effectively protect the trachea of the patient. It can effectively prevent one end of the tracheostomy tube from injuring the trachea of the patient when the conventional tracheostomy tube is mounted. In other words, the tracheostomy tube protecting membrane can effectively avoid trachea injury.

While the invention herein disclosed has been described by means of specific embodiments, numerous modifications and variations could be made thereto by those skilled in the art without departing from the scope and spirit of the invention set forth in the claims.

The invention claimed is:

1. A device for positioning a tracheostomy tube comprising:
   a tracheostomy tube protecting membrane comprising a tearing line portion formed at two sides of the tracheostomy tube protecting membrane, with the tracheostomy tube protecting membrane used for mounting in a trachea of a patient to form a positioning path for the tracheostomy tube, with the tearing line portion being used for torn open and removed, wherein the tracheostomy tube protecting membrane has an end with a first opening and another end with a second opening, with the first opening being greater than the second opening.

2. The device of claim 1, wherein the tracheostomy tube comprises a tube body and a balloon; wherein the tracheostomy tube has a first end and a second end; and wherein the balloon is mounted on the first end of the tracheostomy tube.

3. The device of claim 1, wherein the tracheostomy tube protecting membrane is a plastic membrane.

4. The device of claim 1, wherein the tracheostomy tube has a first length; wherein the tracheostomy tube protecting membrane has a second length; and wherein the second length is greater than the first length.

5. The device of claim 1, further comprising a connector; wherein the connector is mounted on the tracheostomy tube protecting membrane.

* * * * *